(12) United States Patent
Horchler et al.

(10) Patent No.: US 8,350,117 B2
(45) Date of Patent: Jan. 8, 2013

(54) WOUND COVER

(75) Inventors: Harald K. Horchler, Wiehl (DE); Daniela Horchler, Wiehl (DE)

(73) Assignee: Biocell Gesellschaft fuer Biotechnology mbH (DE)

( * ) Notice: Subject to any disclaimer, the term of this patent is extended or adjusted under 35 U.S.C. 154(b) by 714 days.

(21) Appl. No.: 12/306,590

(22) PCT Filed: Jun. 25, 2007

(86) PCT No.: PCT/EP2007/056321
§ 371 (c)(1),
(2), (4) Date: Aug. 3, 2009

(87) PCT Pub. No.: WO2008/000720
PCT Pub. Date: Jan. 3, 2008

(65) Prior Publication Data
US 2009/0306611 A1 Dec. 10, 2009

(30) Foreign Application Priority Data

Jun. 29, 2006 (EP) .................................. 06116313
Jun. 29, 2006 (EP) .................................. 06116317

(51) Int. Cl.
*A61F 13/15* (2006.01)
(52) U.S. Cl. .......................................... 604/360; 607/2
(58) Field of Classification Search .................. 604/304, 604/358, 360; 607/2; 428/113, 297.1, 297.4, 428/300.4, 300.7, 311.51
See application file for complete search history.

(56) References Cited

U.S. PATENT DOCUMENTS

| 5,604,200 A | 2/1997 | Taylor-McCord ................ 514/8 |
| 6,333,093 B1 * | 12/2001 | Burrell et al. ................. 428/194 |
| 2006/0264140 A1 * | 11/2006 | Andrady et al. ............... 442/341 |
| 2007/0059377 A1 * | 3/2007 | Freddo et al. ................. 424/601 |

FOREIGN PATENT DOCUMENTS

| EP | 0378852 | 7/1990 |
| JP | 57021549 | 2/1992 |
| JP | 7054208 | 2/1995 |
| JP | 11200209 | 7/1999 |
| JP | 2009-540988 | 11/2009 |
| WO | WO 94/15623 | 7/1994 |
| WO | WO 02/00268 | 1/2002 |
| WO | WO 02/066085 | 8/2002 |
| WO | WO 03/053484 | 7/2003 |

OTHER PUBLICATIONS

Dalton et al. Electrospinning of polymer melts: Phenomenological observations. Polymer 48 (2007) 6823-6833.*

(Continued)

*Primary Examiner* — Tatyana Zalukaeva
*Assistant Examiner* — Benedict L Hanrahan
(74) *Attorney, Agent, or Firm* — Ohlandt, Greeley, Ruggiero & Perle, LLP

(57) ABSTRACT

A wound cover comprising:
an absorber layer made of a functional non-woven comprising at least first and second filaments;
wherein said first filaments comprise a core of a polyethylene terephthalate and a sheath of polyolefin, and a silver source is incorporated in the sheath; and
wherein said second filaments comprise a core of polyacrylonitrile and a sheath of polyacryl;
wherein the absorber layer is capable of absorbing from 0.15 to 1.20 ml/cm$^2$ of water.

20 Claims, 1 Drawing Sheet

OTHER PUBLICATIONS

O'Neill et al. Antimicrobial properties of silver-containing wound dressings: a microcalorimetric study. International Journal of Pharmaceutics 263 (2003) 61-68.*

Terrill P. et al. Absorption of blood by moist wound healing dressings. Primary Intention 11, 1 (Feb. 2003) 7-17.*

Clark M. Compression bandages: principles and definitions. Understanding compression therapy (2003) 5-7.*

Parsons et al. Silver Antimicrobial Dressings in Wound Management: A Comparison of Antibacterial, Physical, and Chemical Characteristics. Wounds: A Compendium of Clinical Research and Practice, 18, 8 (Aug. 2005) 222-232.*

International Search Report for the corresponding International Patent Application No. PCT/EP07/56321 dated Dec. 11, 2007.

International Search Report for PCT/EP2007/056321 dated Jan. 13, 2009.

European Search Report based on European Application No. EP 06116317 dated Jan. 17, 2007.

* cited by examiner

WOUND COVER

BACKGROUND

1. Field of the Disclosure

The present disclosure relates to a wound cover and the use thereof.

2. Discussion of the Background Art

In the prior art, a wide variety of wound covers are known which have the primary purpose to prevent foreign matter from intruding into a wound and to absorb blood or wound secretion.

A distinction is made between dry wound treatment and wet wound treatment.

Dry wound treatment essentially serves to protect minor injuries and to absorb wound secretion.

In wet wound treatment, it is attempted to create an improved wound healing environment by protecting the wound from drying up and intrusion of germs, wherein an exchange of gases and water vapor is to be ensured if possible. Such wet wound treatment is employed for wounds healing by secondary intention, chronic wounds and occasionally for wounds healing by primary intention.

In wound healing by secondary intention, there is a tissue deficiency leading to gaping wound margins that cannot be closed by suture, clips or the like. It is necessary to promote the proliferation of the body's own tissue in order to cover the wound.

Various materials are being employed to attempt to produce improved wound dressings. Such materials, also referred to as hydroactive dressings, consist, for example, of alginates, of polyurethane-based polymer foams or of fiber filaments, such as carboxymethylcellulose. In part, they are doped with silver ions in order to produce a bactericidal effect. The degree and amount of moisture taken up, the defined release of silver ions and similar parameters define the performance of the products.

Of the products that have been commercially available to date, none are satisfactory, and in part, the materials are not sufficiently stable, i.e., they cannot maintain their consistency after a corresponding uptake of moisture. In part, the release of silver ions is too great, so that silver chloride precipitations occur in the tissue.

Therefore, the disclosure relates to a wound cover that overcomes at least some of the drawbacks of the prior art.

SUMMARY

The wound cover according to the disclosure has an absorber layer made of a functional non-woven comprising at least first and second filaments;
wherein said first filaments comprise a core of a polyethylene terephthalate and a sheath of polyolefin, and a silver source is incorporated in the sheath; and
wherein said second filaments comprise a core of polyacrylonitrile and a sheath of polyacryl;
wherein the absorber layer is capable of absorbing from 0.15 to 1.20 ml/cm$^2$ of water.

DETAILED DESCRIPTION OF THE PREFERRED EMBODIMENT

Figure 1:
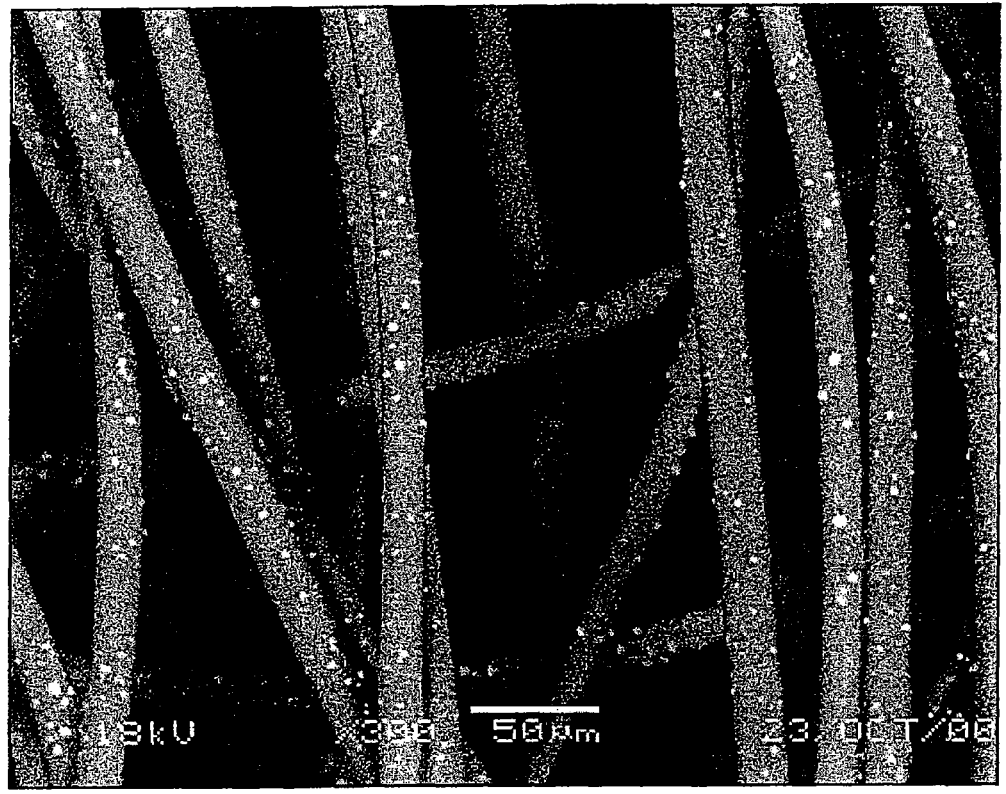
FIG. 1 is a scanning electron micrograph of the fiber.

In a preferred embodiment, the wound dressing has at least two layers, wherein one layer is a layer proximal to the wound consisting of a hydrophobic material having an inside opening width of from 10 to 25 μm.

"Hydrophobic materials" within the meaning of this application are those forming a contact angle with water of more than 90°. In particular, suitable materials include polyolefins, for example, polyethylenes.

The layer proximal to the wound has an inside opening width of from 10 to 25 μm, i.e., the layer is permeable due to the pores. Independently of the exact geometric shape of the opening, the inside opening width is the greatest distance between two points. If the material has pores of different sizes, the defined inside opening width is the mean inside opening width of the pores. Inside opening widths of such dimensions can be readily determined and evaluated by means of a microscope.

One component of the wound cover is an absorber layer consisting of a functional non-woven. The functional non-woven comprises at least two filaments. The first filament has a core of a polyethylene terephthalate and a sheath of a polyolefin. In this sheath, a silver source capable of releasing silver ions has been incorporated.

Suitable polyolefins for the sheath include, for example, polyethylene, polypropylene. The terms "polyethylene" and "polypropylene" include variants, such as HDPE, MDPE, LDPE, LLPE, oriented and biaxially oriented polypropylenes (OPP and BOPP).

For the release of silver ions, the first filament preferably contains silver zeolites fused into the outer sheath and thus firmly integrated. Suitable concentrations of silver zeolite are within a range of from 0.8 to 5% by weight, preferably from 1.5 to 5% by weight, or from 0.8 to 1.5% by weight.

As the second filament, filaments having a core of polyacrylonitrile and a sheath of superabsorbing polyacryl are employed. The absorber layer has a superabsorbing polyacryl material on the outside that preferably consists of a copolymer of polyacrylic acid and polyammonium acrylate.

The absorber layer is capable of absorbing from 0.15 to 1.2 ml of water per cm$^2$ in the absorber layer. The measurement of the absorption of dressing means is described in the standard DIN EN ISO 13726-1.

In one embodiment, the absorber layer is again constituted of several individual layers. The individual layers are made of staple fibers bonded by high density needling and may have different basis weights. The total basis weight of the absorber layer is preferably from about 150 to 350 g/m$^2$, which may be distributed over several layers.

In one embodiment of the disclosure, said at least two filaments of the absorber layer together form a helix; this has a positive effect on the moisture management.

In a further preferred embodiment, the absorber layer is capable of releasing from 10 to 100 μg of silver ions per 100 cm$^2$ of wound cover over a period of 72 hours in contact with water. The test conditions are described in the Example. On the one hand, it is achieved thereby that this concentration is so high as to be effective over this period of time. On the other hand, it is prevented that it is too high, which would cause silver chloride to precipitate in the wound, for example.

The suitable diameter for the filaments is from 5 to 10 μm, the core preferably having a diameter within a range of from 0.5 to 2 μm in one embodiment. By using filaments having a core and sheath, advantageous properties of the respective materials are combined.

In one embodiment, the layer proximal to the wound and the absorber layer are bonded together with an adhesive.

In a preferred embodiment, the wound cover has particularly fast absorbing properties. In this case, the absorber layer can take up 50-70% of its absorption capacity within 10 seconds. It is further advantageous if the wound cover when under pressure releases only a minor proportion of the liquid taken up. Preferably, under a pressure of 3,500 Pa (20 mm Hg), the wound cover retains at least 50% of the water taken up. The test is described in the Example.

Further, it is advantageous for the wound cover to have a low transverse moisture spread rate. A low transverse moisture spread rate means that wetting one spot does not cause the liquid to spread over the entire material. This has the advantage that a contamination between the different areas of the wounds is prevented thereby. Preferably, the transverse moisture spread rate is below 15 mm per 24 hours. The test is described in DIN EN ISO 13726-2.

Further, in the second filament, the fiber preferably does not lose its consistency upon contact with water, i.e., the outer sheath does not become detached from the core. This is defined by demanding that the diameter of the fiber increases to the double at most in water and that no detaching of the layer can be observed macroscopically.

The filaments need not be contained in the same proportion in the absorber layer. Typically, the weight ratio of the first and second filaments of the absorber layer is from 90:10 to 50:50, preferably from 90:10 to 70:30.

The disclosure further relates to the use of the wound cover for treating wounds, especially chronic wounds as caused by reduced microcirculation and reduced oxygen saturation coefficient, free radicals or compression ischemia.

Particularly preferred fields of application for the wound cover according to the disclosure include decubitus, arterial ulcer as may occur in peripheral arterial occlusive disease, venous ulcer as may occur in chronic venous insufficiency, neuropathic ulcer, for example, from diabetic foot syndrome, burns, especially of degree IIa/IIb, postsurgical wounds, radiological wounds (radiation ulcers) as occur, for example, in radiotherapy upon tumor resection. Another field of application is the treatment of bacterially caused wounds and chemically caused wounds, including especially from biological or chemical weapons.

The material according to the disclosure may also be used as a wet electrode. For example, the wound cover may be hydrated with an electrolyte solution, followed by transferring a direct current onto the wound surface by means of an electrode, preferably a double-amplitude monophasic direct current. It has been described that this promotes the formation of vascular epithelial growth factor (VEGF).

Preferably, the treating time is within a range of from 15 min to 24 hours with a pulse rate of from 100 to 120 pulses per second. Preferably, a low pulse rate direct current having a voltage of up to 200 Volts is employed. The powering of such a unit may be effected, for example, by batteries. The typical curve shape of direct current is a monophasic exponential direct current pulse with a fixed pulse interval of 100 μs.

The wound cover may also be employed as a cleaning cloth for cleaning wounds. The release of silver ions enables a bactericidal effect on the environment. The basis weight is preferably within a range of from 40 to 100 g/m².

In a further embodiment, the wound cover may be placed into a washing machine as a pad, for example, by enclosing it in a water-permeable bag. It will then release silver ions in order to prevent the formation of a biofilm in the washing machine. A concentration within a range of from $10^{-6}$ to $10^{-9}$ mol/l in the washing liquor is sufficient for this purpose.

The disclosure further relates to a kit which contains a hyaluronic acid spray in addition to a wound cover according to the disclosure. The kit according to the disclosure has a particularly high efficiency in combination with hyaluronic acid.

The hyaluronic acid spray preferably has the following properties:
 1 to 5 mg/ml of non-cross-linked hyaluronic acid;
 buffer substances and salts for adjusting
  a pH value of 5.5-6.0; and
  an osmolality of from 250 to 350 mOsmol/kg;
 water.

The spray contains from 1 to 5 mg/ml of non-cross-linked hyaluronic acid. An amount of from 1 to 3 mg/ml is preferred. In addition, the spray contains buffer substances and salts to adjust the pH value to a range of from 5.5 to 6.5 and to adjust the osmolality to a range of from 250 to 350 mOsmol/kg.

Osmolality is the number of dissolved particles per kilogram of solution. For example, one mole of sodium chloride yields two Osmol of particles when dissolved in water due to ionization.

The wound spray further contains water.

Suitable non-cross-linked hyaluronic acid preferably has an average molecular weight within a range of from 400 to 600 kDa. In a preferred embodiment, the hyaluronic acid is one prepared by biofermentation rather than one isolated from cockscombs, as frequent in the prior art. Biofermented hyaluronic acid is free from allergenic impurities as frequently contained in products obtained from cockscombs. A particularly suitable strain for the preparation of hyaluronic acid is *Staphylococcus pyogenes* H4489A. The hyaluronic acid may also be employed as a salt, for example, as an Na or K salt.

Biocompatible non-toxic components, for example, sodium chloride, potassium chloride or calcium chloride, are suitable as buffer substances. The adjusting of the pH value may be effected, for example, by buffering with sodium hydrogencarbonate.

A particularly preferred composition corresponds to the known Ringer solution and contains 9 g/l NaCl, 0.2 g/l KCl, 0.2 g/l $CaCl_2$ and 0.1 g/l $NaHCO_3$.

In the wound spray according to the disclosure, further substances may be contained, for example, agents for adjusting the viscosity.

In a preferred embodiment, the wound spray does not contain any further active substances. "Active substances" within the meaning of this application means substances causing an effect through receptors of patients' cells, especially peptide-based substances, such as growth factors.

In another preferred embodiment of the disclosure, the spray is free of preservatives. It has been found that preservatives may have negative effects on wound healing.

According to the disclosure, the spray is employed for spraying on the wound on the whole area thereof. In order to achieve a suitable dosage, the amounts of spray should be low. An amount per spray on the order of from 0.1 to 0.15 ml is particularly suitable.

A suitable viscosity is within a range of from 1 to 8.5 m²/s. Such a viscosity means that the spray is fluid enough that it can be readily sprayed and distributes well, but on the other hand, it is not too fluid, which would cause it to flow off the wound immediately.

The sprayed-on amount of hyaluronic acid dries on within a short period of time and can provide the tissue with important nutrients, for example, salts, due to its further components.

The administration of the spray according to the disclosure results in a particularly unproblematic application without pain to the patient, because no pressure is applied to the wound in contrast to usual compresses etc. In particular, it is advantageous that the hyaluronic acid employed can be absorbed by the body, i.e., it is not necessary to detach the wound dressing that has formed from the wound again.

Surprisingly, it is found that phagocytosis, fibroblast proliferation, cytokine release, cell migration, angiogenesis and collagen synthesis could be enhanced by the spray according to the disclosure.

The wound cover and especially the kit are also suitable for treating hypertrophic tissue and cortisone-damaged skin.

The disclosure is further illustrated by the following Examples.

EXAMPLE 1

Polyethylene terephthalate and polyethylene are molten, and a silver zeolite is added to the polyethylene in an amount of 2.5% by weight. The two polymers are subjected to coextrusion, the polyethylene terephthalate forming the core. By a temperature drop and extension, a fineness of 2.9 dtex is adjusted.

FIG. 1 shows a scanning electron micrograph of the fiber.

The second filament is prepared by coextrusion of polyacrylonitrile and a polyacrylic acid/polyammonium acrylate copolymer.

From the first and second filaments, fragments of 51 mm length are produced, mixed at a weight ratio of 30:70 and projected onto a running rubber roll mill with supersonic speed to form a staple non-woven fabric.

Three layers (25 g/m$^2$, 220 g/m$^2$ and 25 g/m$^2$) of the above mentioned material are placed on top of one another and bonded by needle punching. The textile sheet obtained is coated with a hypoallergenic acrylate adhesive and thermally bonded with a polyolefin. Then, the product is cut and packaged. A final sterilization is effected with ionizing radiation from $^{60}$Co.

EXAMPLE 2

Examination of the Properties

Example 2a: Measurement of Silver Release

The silver ion release was measured by means of ICP-OES (inductively coupled plasma optical emission spectroscopy) analysis. The release rate was 60.15 μg/100 cm$^2$.

Example 2b: Measurement of Absorption Behavior

The measurement of the absorption behavior was effected according to DIN EN 13726-1—Absorption; the test method determines the rating of the absorption properties of a wound cover, taking into account the suction performance plus the transport of the moisture vapor upon contact with the liquid. An absorption capacity of 77.55 g/100 cm$^2$ was obtained.

Example 2c: Determination of Transverse Moisture Spread Rate

The measurement of transverse moisture spread rate was effected according to DIN EN 13726-2—Moisture Vapour Transmission Rate; the test method determines the rating of the moisture vapor transmission rate of permeable sheet composites. A value of 11 mm/24 h was measured.

Example 2d: Measurement of Behavior Under Compressive Pressure

The measurement was effected according to DIN EN 13726.3—Waterproofness; the test method determines the rating of the capability of withstanding a hydrostatic pressure of a 500 mm water column for a period of 300 s. About 70% of the capacity could be retained. In a test with a pressure of 20 mm Hg, 18 g/100 cm$^2$ could be retained.

Example 2e: Mechanical Property

The product had a total weight of about 290 g/m$^2$ and a thickness of 2.5 mm. The longitudinal maximum tensile strength (EN 29073-03) was 31 N/50 mm, and the longitudinal elongation according to EN 29073-03 was 90%.

EXAMPLE 3

Medical grade hyaluronic acid sodium salt obtained by biofermentation was subjected to a quality test. The product had a molecular weight of from 400 to 600 kDa. Its protein content was ≦0.3% by weight, its chloride content was ≦0.5% by weight, and its iron content was ≦80 ppm.

Two grams of hyaluronic acid sodium salt was dissolved in one liter of Ringer solution. The Ringer solution contained 9 g of sodium chloride, 0.2 g of potassium chloride, 0.2 g of calcium chloride, 0.1 g of sodium hydrogencarbonate per 1 liter. The pH value was tested and adjusted to a value of 6.0 using aqueous sodium hydroxide or hydrochloric acid. An osmolality of about 200 mOsmol/kg was obtained.

The finished product was filled into a spraying device (Comod® system).

The product according to the disclosure can be sprayed directly onto the cleaned wound. Depending on the wound size, about two sprays are sufficient.

EXAMPLE 4

Observational Study

A four-week controlled observational study with the wound cover according to the disclosure was performed with 10 patients suffering from chronic venous insufficiency (CVI), changing the dressings three to four times per week. The treatment was effected as a moisture treatment. When the self-hydration is insufficient, it is compensated with Ringer solution. The data of all patients were acquired with a documentation system and recorded. The patients were not especially selected, but corresponded to the normal patients frequenting a practice focusing on ulcer treatment. The evaluation and interpretation of the wounds was effected by analogy with Falanga T.I.M.E.

Table 1 shows essential results of the observational study with 10 patients

| General bases of the results | |
| --- | --- |
| Dressing changes performed with 10 patients | 130 |
| Cumulated treatment/healing time | 327 days |
| Cumulated wound area sizes | 42.2 cm$^2$ |
| Cumulated residual area sizes | 17.6 cm$^2$ |
| Total expenses for all materials (pharmacy gross acquisition price) | 1020.00 € |
| Clinical data | |
| Wound area reduction in % (WR %) in 4 weeks | 62% |
| Residual sizes in % after 4 weeks | 34% |
| Wound area reduction per week in % | 15.5% |
| Median wound area reduction per day | 0.144 cm$^2$/day |
| Time to heal per cm$^2$ | 6.92 days |
| Healed wounds per week | 7.5% |

One of the patients initially showed a particularly large wound area. If this patient is excluded from the result, the following evaluation is obtained.

| General bases of the results | |
| --- | --- |
| Dressing changes performed with 10 patients | 126 |
| Cumulated treatment/healing time | 292 days |
| Cumulated wound area sizes | 17.2 cm$^2$ |
| Cumulated residual area sizes | 2.6 cm$^2$ |
| Total expenses for all materials (pharmacy gross acquisition price) | 978.00 € |
| Clinical data | |
| Wound area reduction in % (WR %) in 4 weeks | 85% |
| Residual sizes in % after 4 weeks | 15% |
| Wound area reduction per week in % | 21.2% |
| Median wound area reduction per day | 0.059 cm$^2$/day |
| Time to heal per cm$^2$ | 16.97 days |
| Healed wounds per week | 8.33% |

Result

The dressing according to the disclosure is suitable for achieving a wound area regression of more than 60% in four weeks in chronic wounds.

Figure 2:
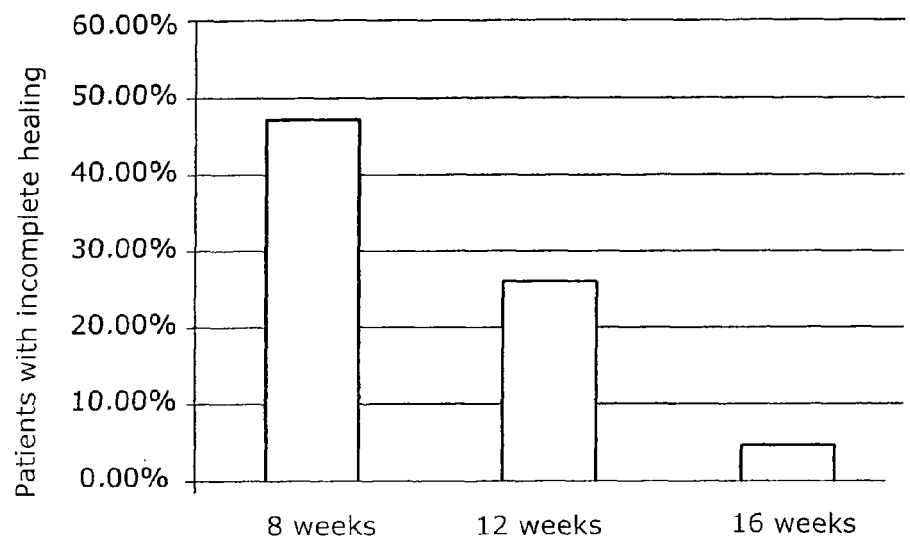
FIG. 2 is a graph plotting patients with incomplete healing versus time.

FIG. 2 shows a healing analysis. It is found that the time to heal is 8 weeks in about 50% of the cases, and 75% of all cases healed in 12 weeks.

What is claimed is:

1. A wound cover comprising:
an absorber layer made of a functional non-woven comprising at least first and second filaments;
wherein said first filament comprises a core of a polyethylene terephthalate and a sheath of polyolefin, and a silver source is incorporated in the sheath;
wherein said second filament comprises a core of polyacrylonitrile and a sheath of a compound comprising a polyacrylic material; and
wherein the absorber layer is capable of absorbing from 0.15 to 1.20 ml/cm$^2$ of water.

2. The wound cover according to claim 1, wherein said wound cover comprises at least two layers including a layer proximal to the wound consisting of a hydrophobic material having a pore with an inside opening width of from 10 to 25 μm.

3. The wound cover according to claim 2, wherein said layer proximal to the wound consists of a polyolefin, especially polyethylene.

4. The wound cover according to claim 1, wherein the two filaments of the absorber layer together form a helix.

5. The wound cover according to claim 1, wherein the absorber layer releases from 10 to 100 μg of silver ions per 100 cm$^2$ of wound cover over a period of 72 hours upon contact with water.

6. The wound cover according to claim 1, wherein said first and second filaments independently have a diameter of from 5 to 20 μm.

7. The wound cover according to claim 1, wherein said first and second filaments independently have a core having a diameter of from 0.5 to 2 μm.

8. The wound cover according to claim 2, wherein said layer proximal to the wound and the absorber layer are bonded together with an adhesive.

9. The wound cover according to claim 1, wherein from 50 to 70% of the absorption capacity can be taken up within 30 seconds.

10. The wound cover according to claim 1, wherein at least 50% of the capacity can be retained under a compressive pressure of 20 mm Hg.

11. The wound cover according to claim 1, wherein the transverse moisture spread rate is from 5 to 15 mm in 24 hours.

12. The wound cover according to claim 1, wherein said fiber filaments maintain their consistency.

13. The wound cover according to claim 1, wherein said first and second filaments are in a weight ratio of from 1:3 to 3:1.

14. A method for treating a wound by applying said wound cover according to claim 1 to said wound.

15. The method according to claim 14 wherein said wound is chronic.

16. A kit containing a wound cover according to claim 1 and a spray containing hyaluronic acid.

17. The method according to claim 14 wherein said wound is at least one selected from the group consisting of: decubitus, arterial ulcer, venous ulcer, neuropathic ulcer, burns, especially burns of degree IIa/IIb, postsurgical wounds, radiological wounds (radiation ulcers), bacterially caused wounds, and chemically caused wounds.

18. A wet electrode which comprises said wound cover according to claim 1.

19. A washing glove which comprises said wound cover according to claim 1.

20. A washing pad which comprises said wound cover according to claim 1.

* * * * *